United States Patent [19]

Gutman

[11] 4,176,121

[45] Nov. 27, 1979

[54] 1,3-OXAZOLE PHOSPHATES AND PHOSPHONATES

[75] Inventor: Arnold D. Gutman, Berkeley, Calif.

[73] Assignee: Stauffer Chemical Company, Westport, Conn.

[21] Appl. No.: 954,495

[22] Filed: Oct. 25, 1978

Related U.S. Application Data

[62] Division of Ser. No. 850,764, Nov. 11, 1977, Pat. No. 4,137,308.

[51] Int. Cl.$^2$ .................. C07D 263/32; C07D 263/46
[52] U.S. Cl. ................................. 548/119; 424/200; 548/228; 548/235
[58] Field of Search .................................. 260/307 R

[56] References Cited

U.S. PATENT DOCUMENTS 4,137,308  1/1979  Gutman ........................ 260/307 R

*Primary Examiner*—Jose Tovar
*Attorney, Agent, or Firm*—Joel G. Ackerman

[57] ABSTRACT

Compounds having the formula

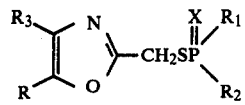

in which R is phenyl, phenylthio, phenoxy, or lower aklylthio; $R_1$ is lower alkoxy; $R_2$ is lower alkyl or lower alkoxy; $R_3$ is lower alkyl; and X is sulfur or oxygen. The compounds have utility as insecticides and miticides.

The compounds can be prepared through novel intermediates having the formula

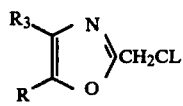

by a novel process of reacting a methyl ketone oxime with a haloacetyl chloride in the absence of an acid acceptor.

3 Claims, No Drawings

1,3-OXAZOLE PHOSPHATES AND PHOSPHONATES

This is a division of application Ser. No. 850,764, filed Nov. 11, 1977, now U.S. Pat. No. 4,137,308, issued 1-30-1979.

SUMMARY OF THE INVENTION

This invention relates to novel compounds having the formula

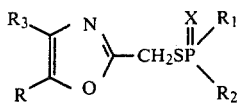

in which R is phenyl, phenylthio, phenoxy, or lower alkylthio; $R_1$ is lower alkoxy; $R_2$ is lower alkyl or lower alkoxy; $R_3$ is lower alkyl and X is sulfur or oxygen, provided that when R is isopropylthio, $R_3$ is a lower alkyl group containing from 1 to 3 carbon atoms, and a novel process and intermediates for preparing such compounds.

As will be shown from the data which follows herein, the compounds have shown activity as insecticides and miticides.

In one embodiment, $R_2$ is lower alkyl; the compounds are phosphonates. In another embodiment $R_2$ is lower alkoxy; the compounds are phosphates. In a preferred embodiment, R is lower alkylthio.

In another aspect, this invention relates to a method of controlling or combatting insects or mites by applying an insecticidally or miticidally effective amount of a compound as defined herein to the insect or mite or the locus thereof.

In yet another aspect, this invention relates to an insecticidal or miticidal composition of matter comprising an insecticidally or miticidally effective amount of a compound as defined herein, with an inert carrier or diluent.

By the terms "lower alkyl", "lower alkoxy", and "lower alkylthio" are meant such groups containing from 1 to 6, preferably from 1 to 4, carbon atoms. Examples of such groups are: methyl, ethyl, n-propyl, isopropyl, n-butyl, isobutyl, sec.-butyl, and tert.-butyl; methoxy, ethoxy; methylthio, ethylthio, n-propylthio, isopropylthio, n-butylthio, sec.-butylthio, isobutylthio, tert.-butylthio and the like.

The novel compounds of this invention are advantageously prepared via novel intermediates having the general formula

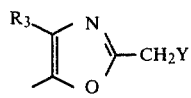

in which R and $R_3$ are as defined hereinabove and Y is chloro or bromo, provided that when R is isopropylthio, $R_3$ is $C_1$-$C_3$ lower alkyl. Preferably R is arylthio or lower alkylthio.

In general, the oxazole ring is conventionally prepared by condensation of an alpha-haloketone with an appropriate amide, as described in the article by Bredereck and Gompper, *Berichte* 87, 700 (1954). However, it has now been found that the novel intermediates can also be prepared by reaction of a specified type of methyl ketone oxime as described herein with a chloroacetyl chloride or bromide:

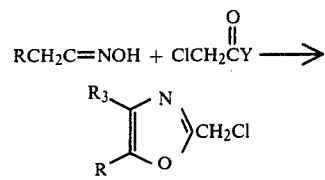

when the reaction is conducted in the presence of a substantial stoichiometric excess of the acyl halide and in the absence of an acid acceptor or base. By the term "substantial stoichiometric excess" is meant a two-to-ten fold, preferably two-to-five fold, stoichiometric excess of chloroacetyl chloride or bromide with respect to the oxime.

The intermediate chloromethyl (substituted) oxazole is reacted with an alkali metal (preferably potassium) salt of a thio- or dithiophosphonic or phosphoric acid or with the acid itself to produce the desired final product:

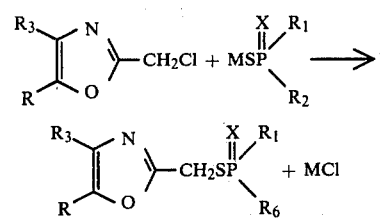

(R, $R_1$, $R_2$ and $R_3$ are as defined hereinabove; M represents an alkali metal cation).

In the prior art, as exemplified in U.S. Pat. Nos. 3,732,306; 3,733,419 and 3,885,043, reactions between ketone oximes and acyl halides were conducted in the presence of an acid acceptor such as pyridine or triethylamine and optionally with equal amounts of reactants or a slight excess of acyl halide. When conducted in such a manner, however, the reaction which occurred was acylation of the oxime. It has now been found surprisingly, that when a methyl ketone oxime as defined herein is reacted with a chloroacetyl chloride or bromide in the absence of an acid acceptor and with the use of a substantial excess of the acyl halide, a substituted oxazole can be formed. It appears preferable for oxazole ring formation that R be a group such as aryl, aryloxy, arylthio or, most preferably, alkylthio. R could also contain a sulfone or sulfoxide subgroup. The reaction is conducted in the absence of an acid acceptor; the presence of a small amount of acid acceptor would result in the formation of a corresponding amount of non-oxazole impurity. In addition to chloroacetyl halides, di- and trichloroacetyl halides could also be utilized to produce corresponding di- and trichloromethyl oxazoles in the same manner.

More particularly, a methyl ketone oxime having the formula

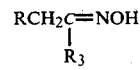

in which R is phenyl, phenylthio, phenoxy or lower alkylthio, is continuously added to a 2-10-fold, preferably 2-5-fold, excess of chloroacetyl chloride or bromide. A vigorous reaction ensues, with evolution of HCl gas. After standing for one hour, the reaction mass is heated on a steam bath until HCl evolution ceases and is then stripped under vacuum to remove excess acyl halide. The residue is poured into a 5% aqueous solution of sodium bicarbonate; the aqueous mixture is extracted with a solvent such as benzene; the extract is dried and the solvent stripped off under vacuum to yield the intermediate chloromethyl (substituted) oxazole.

The intermediate is then combined with an alkali metal salt, preferably a potassium salt, of a thio- or dithiophosphonic or -phosphoric acid in a solvent such as acetone, to produce the final desired compound.

The following are representative examples of preparation of the insecticidal compounds of this invention as well as examples of the novel intermediates and process for their preparation.

EXAMPLE 1

A. In a 200 ml. flask equipped with a stirrer was placed 50 ml. (0.31 mole) of chloroacetyl chloride. 14.7 g. (0.123 mole) methylthioacetone oxime was slowly added. A very exothermic reaction occurred with each addition of oxime. When the reaction temperature reached 65° C., small portions of benzene (total, 25 ml.) were added to moderate the temperature. After the oxime had all been introduced, the reaction mixture was heated under reflux on a steam bath for 2½ hours. The reaction mass was then stripped in vacuo and the residue added to a solution of sodium bicarbonate, with stirring. The crude product was extracted with benzene and treated with carbon. The carbon was removed by filtration. The benzene phase was separated, again treated with carbon, and benzene was removed under vacuum to yield 14.3 g. of 2-chloromethyl-4-methyl-5-methylthio-1,3-oxazole (Intermediate A in Table II), $n_D^{30}$ 1.5075.

B. The potassium salt of O,O-dimethyl dithiophosphoric acid was prepared by combining 3.2 g (0.02 mole) of the acid with excess potassium carbonate in 75 ml. acetone. The acetone solution of the salt was then decanted into a solution of 2.5 g. (0.014 mole) of the intermediate prepared in step A, in acetone. Potassium chloride precipitation commenced immediately. The mixture was let stand for 1 hour at room temperature, then poured into 250 ml. benzene and washed with 2 portions, each of 200 ml., of water. The benzene phase was separated, dried and evaporated under vacuum. There were obtained 3.8 g. (90.8% of theoretical) of 2-(O,O-dimethylphosphorodithioylmethyl)-4-methyl-5-methylthio-1,3-oxazole (Compound 6 herein), $n_D^{30}$ 1.5377.

EXAMPLE 2

A. Similarly to Example 1A, 5 g. (0.034 mole) of isopropylthio acetone oxime was combined with 10 ml. (0.062 mole) of chloroacetyl chloride to yield 6.3 g. of 2-chloromethyl-4-methyl-5-isopropylthio-1,3-oxazole, (Intermediate B in Table II), $n_D^{30}$ 1.4970. Five ml. of benzene was used to moderate temperature.

B. Similarly to Example 1B, 3 g. (0.014 mole) of 2chloromethyl-5-isopropylthio-1,3-oxazole, 3.2 g. (0.02 mole) of O,O -dimethyldithiophosphoric acid and 3 g. K$_2$CO$_3$ in 75 ml. acetone were combined to yield 4.3 g. (94% of theoretical) of 2-(O,O-dimethylphosphorodithioylmethyl)-4-methyl-5-isopropylthio-1,3oxazole (Compound 9 herein), $n_D^{30}$ 1.5250.

EXAMPLE 3

Similarly to Example 2B, 3 g. (0.014 mole) of 2-chloromethyl-4-methyl-5-isopropylthio-1,3-oxazole, 3.4 g. (0.02 mole) of O-ethyl, ethyl dithiophosphonic acid and 3 g. of K$_2$CO$_3$ in 75 ml. acetone yielded 4.4 g. (93% of theoretical) of 2-(O-ethyl, ethylphosphonodithioylmethyl)-4-methyl-5-isopropylthio-1,3-oxazole (Compound 10 herein), $n_D^{30}$ 1.5392.

EXAMPLE 4

A. Similarly to Example 1A, 5 g. (0.0335 mole) of phenyl acetone oxime was combined with 10 ml. (0.062 mole) of chloroacetyl chloride to yield 7.0 g. of 2-chloromethyl-4-methyl-5-phenyl-1,3-oxazole, (Intermediate G in Table II), b.p. 125°–130° C., $n_D^{30}$ 1.5577. Five ml. of benzene was used to moderate temperature.

B. Similarly to Example 1B, 2.5 g. (0.012 mole) of 2-chloromethyl-4-methyl-5-phenyl-1,3-oxazole, 2.8 g. (0.015 mole) of O,O-diethyldithiophosphoric acid and excess K$_2$CO$_3$ were combined, yielding 4.2 g. (89.9% of theoretical) of 2-(O,O-diethylphosphorodithioylmethyl)-4-methyl-5-phenyl-1,3-oxazole (Compound 1 herein), $n_D^{30}$ 1.5555.

EXAMPLE 5

A. Similarly to Example 1A, 5 g. (0.027 mole) of phenylthio acetone oxime was combined with 20 ml. (0.124 mole) dichloroacetyl chloride to yield 4.7 g. of 2-chloromethyl-4-methyl-5-phenylthio-1,3-oxazole (Intermediate I in Table II), $n_D^{30}$ 1.5113. Ten ml. of benzene was used to moderate temperature.

B. Similarly to Example 1B, 1.6 g. (0.006 mole) of 2-chloromethyl-4-methyl-5-phenylthio-1,3-oxazole, 3 g. (0.016 mole) of O,O-diethyldithiophosphoric acid and 3 g. K$_2$CO$_3$ in 50 ml. acetone were combined to yield 2.2 g. (95% of theoretical) of 2-(O,O-diethylphosphorodithioylmethyl)-4-methyl-5-phenylthio-1,3-oxazole (Compound 7 herein), $n_D^{30}$ 1.5560.

The following Table I contains some representative insecticidal compounds of this invention.

TABLE I $$R_3 \underset{R}{\overset{N}{\diagup}} \hspace{-6pt} \diagdown \hspace{-6pt} \underset{O}{\diagup} - CH_2SP \overset{X}{\underset{R_2}{\diagdown}} R_1$$

| Compound No. | R | R$_1$ | R$_2$ | R$_3$ | X | m.p. °C. or $n_D^{30}$ |
|---|---|---|---|---|---|---|
| 1 | C$_6$H$_5$ | OC$_2$H$_5$ | OC$_2$H$_5$ | CH$_3$ | S | 1.5555 |
| 2 | C$_6$H$_5$ | OC$_2$H$_5$ | C$_2$H$_5$ | CH$_3$ | S | 1.5625 |
| 3 | C$_6$H$_5$ | OCH$_3$ | OCH$_3$ | CH$_3$ | S | 1.5608 |
| 4 | CH$_3$S | OC$_2$H$_5$ | OC$_2$H$_5$ | CH$_3$ | S | 1.5245 |
| 5 | CH$_3$S | OC$_2$H$_5$ | C$_2$H$_5$ | CH$_3$ | S | 1.5420 |
| 6 | CH$_3$S | OCH$_3$ | OCH$_3$ | CH$_3$ | S | 1.5377 |
| 7 | C$_6$H$_5$S | OC$_2$H$_5$ | OC$_2$H$_5$ | CH$_3$ | S | 1.5560 |
| 8 | i-C$_3$H$_7$S | OC$_2$H$_5$ | OC$_2$H$_5$ | CH$_3$ | S | 1.5137 |
| 9 | i-C$_3$H$_7$S | OCH$_3$ | OCH$_3$ | CH$_3$ | S | 1.5250 |
| 10 | i-C$_3$H$_7$S | OC$_2$H$_5$ | C$_2$H$_5$ | CH$_3$ | S | 1.5392 |
| 11 | C$_6$H$_5$O | OC$_2$H$_5$ | OC$_2$H$_5$ | CH$_3$ | S | 1.5300 |
| 12 | t-C$_4$H$_9$S | OC$_2$H$_5$ | OC$_2$H$_5$ | CH$_3$ | S | 1.5161 |
| 13 | t-C$_4$H$_9$S | OCH$_3$ | OCH$_3$ | CH$_3$ | S | 1.5222 |
| 14 | t-C$_4$H$_9$S | OC$_2$H$_5$ | C$_2$H$_5$ | CH$_3$ | S | 1.5304 |
| 15 | C$_2$H$_5$S | OCH$_3$ | OCH$_3$ | CH$_3$ | S | 1.5288 |
| 16 | C$_2$H$_5$S | OC$_2$H$_5$ | OC$_2$H$_5$ | CH$_3$ | S | 1.5168 |
| 17 | C$_2$H$_5$S | OC$_2$H$_5$ | C$_2$H$_5$ | CH$_3$ | S | 1.5345 |
| 18 | C$_2$H$_5$S | OC$_2$H$_5$ | OC$_2$H$_5$ | CH$_3$ | O | 1.4918 |
| 19 | n-C$_4$H$_9$S | OC$_2$H$_5$ | C$_2$H$_5$ | CH$_3$ | S | (dark oil) |
| 20 | n-C$_4$H$_9$S | OC$_2$H$_5$ | OC$_2$H$_5$ | CH$_3$ | S | (dark oil) |
| 21 | n-C$_3$H$_7$S | OC$_2$H$_5$ | OC$_2$H$_5$ | CH$_3$ | S | 1.5062 |
| 22 | n-C$_3$H$_7$S | OC$_2$H$_5$ | C$_2$H$_5$ | CH$_3$ | S | 1.5255 |
| 23 | i-C$_4$H$_9$S | OC$_2$H$_5$ | OC$_2$H$_5$ | CH$_3$ | S | 1.5030 |

TABLE I-continued $$\underset{R}{\overset{R_3}{>}}\!\!=\!\!\underset{O}{\overset{N}{>}}\!\!-\!\!CH_2SP\!\!\overset{X}{\underset{R_2}{\overset{\|}{<}}}\!\!\overset{R_1}{}$$

| Compound No. | R | $R_1$ | $R_2$ | $R_3$ | X | m.p. °C. or $n_D^{30}$ |
|---|---|---|---|---|---|---|
| 24 | i-$C_4H_9S$ | $OC_2H_5$ | $C_2H_5$ | $CH_3$ | S | 1.5200 |
| 25 | $CH_3S$ | $OC_2H_5$ | $OC_2H_5$ | t-$C_4H_9$ | S | 1.5048 |
| 26 | $CH_3S$ | $OCH_3$ | $OCH_3$ | t-$C_4H_9$ | S | 1.5150 |
| 27 | $C_2H_5S$ | $OC_2H_5$ | $OC_2H_5$ | t-$C_4H_9$ | S | 1.5020 |
| 28 | $C_2H_5S$ | $OCH_3$ | $OCH_3$ | t-$C_4H_9$ | S | 1.5094 |

Table II includes some representative novel intermediates prepared according to the novel process described above.

TABLE II $$\underset{R}{\overset{R_3}{>}}\!\!=\!\!\underset{O}{\overset{N}{>}}\!\!-\!\!CH_2Cl$$

| Intermediate | R | $R_3$ | $n_D^{30}$ |
|---|---|---|---|
| A | $CH_3S$ | $CH_3$ | 1.5075 |
| B | i-$C_3H_7S$ | $CH_3$ | 1.4970 |
| C | t-$C_4H_9S$ | $CH_3$ | 1.5030 |
| D | $C_2H_5S$ | $CH_3$ | 1.4976 |
| E | $CH_3S$ | t-$C_4H_9$ | 1.4830 |
| F | $C_2H_5S$ | t-$C_4H_9$ | 1.4815 |
| G | $C_6H_5$ | $CH_3$ | 1.5577 |
| H | $C_6H_5S$ | $CH_3$ | 1.5113 |
| I | $C_6H_5O$ | $CH_3$ | |
| J | n-$C_4H_9S$ | $CH_3$ | (dark oil) |
| K | n-$C_3H_7S$ | $CH_3$ | |
| L | i-$C_4H_9S$ | $CH_3$ | |

INSECTICIDAL EVALUATION

The compounds in the foregoing Table I were tested for insecticidal activity by the following procedures:

Housefly [*Musca domestica* (Linn.)]: Test compounds were diluted in acetone and aliquots pipetted onto the bottom of 55×15 mm. aluminum dishes. To insure even spreading of the chemical on the bottom of the dishes, 1 ml. of acetone containing 0.02% peanut oil was also added to each dish. After all solvents had evaporated, the dishes were placed in circular cardboard cages containing 25 female houseflies, one to two days old. The cages were covered on the bttom with cellophane and on the top with tulle netting, and each contained a sugar-water saturated cotton plug for maintenance of the flies. Mortality was recorded after 48 hours. Test levels ranged from 100 μg/25 female houseflies down to that at which approximately 50% mortality occurred. The LD-50 values are expressed below in Table III under the heading "HF", in terms of μg of the test compound per 25 female flies.

Black Bean Aphid [*Aphis fabae* (Scop.)]: Nasturtium plants (*Tropaeolum sp.*), approximately 5 cm. tall, were transplanted into sandy loam soil in 3-inch clay pots and infested with 25–50 black bean aphids of mixed ages. 24 hours later, they were sprayed, to the point of runoff, with 50–50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table III under the heading "BA" in terms of percent of the test compound in the sprayed solution.

Green Peach Aphid [*Myzur persicae* (Sulzer)]: Radish plants (*Rhaphanus sativus*), approximately 2 cm. tall, were transplanted into sandy loam soil in 3-inch clay pots and infested with 25–50 green peach aphids of mixed ages. 24 hours later, they were sprayed, to the point of runoff with 50–50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table III under the heading "GPA" in terms of percent of the test compound in the sprayed solution.

German Cockroach [*Blatella germanica* (Linn.)]: Test compounds were diluted in a 50–50 acetone-water solution. 2 cc. of the solution were sprayed through a DeVilbiss type EGA hand spray gun into circular cardboard cages containing 10 one-month old German cockroach nymphs. The test cages were covered on the bottom with cellophane and on the top with tulle netting. Percent mortality was recorded 4 days later. Test concentrations ranged from 0.1% down to that at which approximately 50% mortality occurred. LD-50 values are expressed below in Table III under the heading "GR" in terms of percent of the test compound in the sprayed solution.

Lygus Bug [*Lygus hesperus* (Knight)]: Test compounds were diluted in a 50–50 acetone-water solution. 2 cc. of the solution were sprayed through a DeVilbiss type EGA hand spray gun into circular cardboard cages containing 1 string bean pod and 10 adult lygus bugs. The test cages were covered on the bottom with cellophane and on top with tulle netting. Percent mortality was recorded 48 hours later. Test concentrations ranged from 0.05% dwn to that at which approximately 50% mortality occurred. LD-50 values are expressed below in Table III under the heading "LB" in terms of percent of the test compound in the sprayed solution.

Saltmarsh Caterpillar [*Estigmene acrea* (Druryl)]: Test compounds were diluted in a 50–50 acetone-water solution. Sections of curly dock (*Rumex crispus*) leaves, approximately 1×1.5 inches, were immersed in the test solution for 2–3 seconds and placed on a wire screen to dry. The dried leaves were placed in petri dishes containing a moistened piece of filter paper and infested with 5 second-instar saltmarsh larvae. Mortality of the larvae was recorded 48 hours later, and a piece of synthetic media was added to dishes containing survivors. These were then held for 5 additional days to observe for any delayed effects of the test chemicals.

Test concentrations ranged from 0.05% down to that at which approximately 50% mortality occurred. LD-50 values are expressed below in Table III under the heading "SMC" in terms of percent of the test compound in the solution.

Cabbage Looper [*Trichloplusia ni* (Hubner)]: Test compounds were diluted in a 50–50 acetone-water solution. Cotyledons of hyzini squash (*Calabacita abobrinha*), approximately 1×1.5 inches, were immersed in the test solutions for 2–3 seconds and placed on a wire screen to dry. The dried leaves were placed in petri dishes containing a moistened piece of filter paper and infested with five second-instar cabbage looper larvae. Mortality of the larvae was recorded 48 hours later, and a piece of synthetic media added to dishes containing survivors. These were then held for five additional days to observe for any delayed effects of the test chemicals. terms Test concentrations ranged from 0.1% to that at which approximately 50% mortality occurred. LD-50 values are expressed below in Table III under the heading "CL" in terms of percent of the test compound in the solution.

Tobacco Budworm [*Heliothis virescens* (Fabricius)]: Test compounds were diluted in a 50-50 acetone-water solution. Sections of Romaine lettuce (*Latuca sativa*) leaves, approximately 1×1.5 inches, were immersed in the test solutions for 2–3 seconds and placed on a wire screen to dry. The dried leaves were placed in petri dishes containing a moistened piece of filter paper and infested with five second-instar tobacco budworm larvae. Mortality of the larvae was recorded 48 hours later, and a piece of synthetic media added to dishes containing survivors. These were then held for five additional days to observe for any delayed effects of the test chemicals.

Test concentrations ranged from 0.1% to that at which approximately 50% mortality occurred. LD-50 values are expressed below in Table III under the heading "TBW" in terms of percent of the test compound in the solution.

Southern House Mosquito Larvae [*Culex pipiens quinquefasciatus* (Say)]: Insecticidal activity was determined using third instar larvae of the mosquito *Culex pipiens quinquefasciatus*. Ten larvae were placed in a six ounce, cup containing 100 ml. of an aqueous solution of the test chemical. The treated larvae were stored at 70° F., and 48 hours later the mortality was recorded. Test concentrations ranged from 1.0 ppm down to that at which approximately 50% mortality occurred. LD-50 values are expressed below in Table III under the heading "MOS" in terms of ppm of the test compound in the solution.

MITICIDAL EVALUATION

The compounds in Table I were tested for miticidal activity according to the following procedures:

Two-spotted Mite [*Tetranychus urticae* (Koch)]: The two-spotted mite (2SM), was employed in tests for miticides. The test procedure was as follows:

Pinto bean plants (*Phaseolus sp.*) approximately 10 cm. tall, were transplanted into sandy loam soil in 3-inch clay pots and thoroughly infested with two-spotted mites of mixed ages and sexes. 24 hours later, the infested plants were inverted and dipped for 2–3 seconds in 50-50 acetone-water solutions of the test chemicals. Treated plants were held in the greenhouse, and 7 days later mortality was determined for both the adult mites and the nymphs hatching from eggs which were on the plants at the time of treatment. Test concentrations ranged from 0.05% down to that at which 50% mortality occurred. LD-50 values are expressed below in Table III under the headings "2SM-PE" (i.e., post-embryonic) and "2SM-EGGS", in terms of percent concentration of the test compound in the solution.

SYSTEMIC EVALUATION

The compounds in Table I were tested for systemic aphicidal and miticidal activity according to the following procedure:

Black Bean Aphid: (Systemic) Test chemicals were diluted in acetone and aliquots thoroughly mixed into 500 grams of dry sandy loam soil. The treated soil was placed in a pint-sized carton and a nasturtium plant (*Tropaeolum sp.*) approximately 5 cm. tall was transplanted into each carbon. The plants were then infested with approximately 25 black bean aphids of mixed ages and placed in the greenhouse. 7 days later mortality was recorded. Test concentrations ranged from 10 ppm down to that at which approximately 50% mortality occurred.

Two-Spotted Mite: (Systemic) Test chemicals were dissolved in acetone and aliquots diluted in 200 cc. of water in glass bottles. 2 pinto bean plants (*Phaseolus sp.*) with expanded primary leaves, were supported in each bottle by cotton plugs, so that their roots and stems were immersed in the treated water. The plants were then infested with 75–100 two-spotted mites of various ages and sexes. One week later the mortality of the adult mites and nymphs was recorded. Test concentrations in the water ranged from 10 ppm down to that at which 50% mortality occurred.

LD-50 values are expressed in Table III under the headings "BA-S" and "2SM-SYST." respectively, in terms of percent concentration of the test compound.

TABLE III

| Compound No. | HF, μg | BA, % | BA(S) ppm | GPA, % | GR, % | LB, % | SMC, % | CL, % | TBW, % | MOS, ppm | 2-SM PE, % | EGGS, % | SYST., ppm |
|---|---|---|---|---|---|---|---|---|---|---|---|---|---|
| 1 | 100 | 0.003 | >10 | 0.03 | >0.1 | >0.05 | >0.05 | 0.1 | 0.1 | 0.8 | 0.01 | 0.03 | >10 |
| 2 | 28 | 0.0005 | >10 | 0.002 | >0.1 | >0.05 | 0.05 | 0.1 | >0.1 | 0.2 | 0.001 | 0.01 | >10 |
| 3 | 39 | 0.005 | >10 | 0.03 | >0.1 | >0.05 | 0.05 | 0.1 | >0.1 | >1 | >0.05 | >0.05 | >10 |
| 4 | 24 | 0.0005 | >10 | 0.003 | 0.01 | 0.003 | 0.05 | 0.1 | 0.1 | 0.04 | 0.001 | 0.03 | 2 |
| 5 | 8 | 0.0002 | >10 | 0.002 | 0.01 | 0.002 | >0.05 | >0.1 | 0.01 | 0.05 | 0.0003 | 0.002 | 0.5 |
| 6 | 28 | 0.0005 | >10 | 0.002 | 0.03 | 0.002 | >0.05 | >0.1 | >0.1 | 0.05 | 0.003 | 0.005 | 0.5 |
| 7 | 31 | 0.002 | >10 | 0.003 | >0.1 | 0.5 | >0.05 | >0.1 | >0.1 | 0.2 | 0.008 | 0.005 | >10 |
| 8 | 29 | 0.0005 | >10 | 0.005 | >0.1 | >0.05 | >0.05 | >0.1 | >0.1 | 0.3 | 0.0008 | 0.005 | 2 |
| 9 | 30 | 0.002 | >10 | 0.008 | >0.1 | 0.05 | 0.05 | 0.1 | >0.1 | 0.2 | 0.002 | 0.03 | 2 |
| 10 | 17 | 0.0002 | >10 | 0.001 | 0.05 | 0.01 | 0.03 | 0.03 | >0.1 | 0.08 | 0.0003 | 0.005 | 3 |
| 11 | >100 | 0.002 | >10 | 0.03 | >0.1 | >0.05 | >0.05 | >0.1 | >0.1 | >1 | 0.008 | 0.01 | >10 |
| 12 | 29 | 0.003 | >10 | 0.005 | >0.1 | >0.05 | 0.3 | >0.1 | >0.1 | 0.4 | 0.001 | 0.005 | 10 |
| 13 | 25 | 0.003 | >10 | 0.005 | >0.1 | 0.05 | >0.05 | >0.1 | >0.1 | 0.2 | 0.05 | >0.05 | 10 |
| 14 | 26 | 0.0003 | >10 | 0.0008 | 0.03 | >0.05 | 0.008 | >0.1 | >0.1 | 0.1 | 0.0008 | 0.0005 | 2 |
| 15 | 28 | 0.0003 | >10 | 0.002 | 0.02 | 0.005 | >0.05 | 0.1 | >0.1 | 0.008 | 0.03 | >0.05 | 1 |
| 16 | 30 | 0.0003 | >10 | 0.003 | 0.01 | 0.008 | 0.05 | >0.1 | >0.1 | 0.03 | 0.003 | 0.008 | 2 |
| 17 | 27 | 0.0002 | 8 | 0.002 | 0.01 | 0.003 | 0.05 | 0.02 | 0.1 | 0.02 | 0.001 | 0.005 | 2 |
| 18 | 28 | 0.0005 | 2 | 0.005 | >0.1 | 0.05 | >0.05 | >0.1 | >0.1 | 0.1 | <0.0003 | 0.03 | 2 |
| 19 | 30 | 0.0002 | 2 | 0.002 | 0.05 | >0.05 | >0.05 | >0.1 | >0.1 | 0.08 | 0.001 | 0.005 | 2 |
| 20 | 31 | 0.002 | >10 | 0.005 | >0.1 | >0.05 | 0.05 | >0.1 | >0.1 | 0.2 | 0.003 | 0.008 | 8 |
| 21 | 30 | 0.0005 | >10 | 0.005 | 0.08 | 0.05 | >0.05 | 0.1 | >0.1 | 0.04 | 0.002 | 0.005 | 5 |
| 22 | 30 | 0.0002 | 5 | 0.002 | 0.03 | 0.009 | 0.05 | 0.1 | 0.1 | 0.01 | 0.002 | 0.03 | 2 |
| 23 | 31 | 0.001 | 5 | 0.005 | >0.1 | >0.05 | >0.05 | >0.1 | >0.1 | 0.2 | 0.003 | 0.005 | >10 |
| 24 | 27 | 0.0002 | >10 | 0.002 | 0.08 | >0.05 | 0.05 | >0.1 | >0.1 | 0.03 | 0.002 | 0.005 | 2 |

TABLE III-continued

| Compound No. | HF, μg | BA, % | BA(S) ppm | GPA, % | GR, % | LB, % | SMC, % | CL, % | TBW, % | MOS, ppm | 2-SM PE, % | EGGS, % | SYST., ppm |
|---|---|---|---|---|---|---|---|---|---|---|---|---|---|
| 25 | 27 | 0.0008 | >10 | 0.03 | >0.1 | 0.05 | 0.01 | >0.1 | >0.1 | 0.04 | 0.008 | 0.03 | 5 |
| 26 | 17 | 0.002 | >10 | 0.01 | 0.1 | 0.007 | >0.05 | >0.1 | >0.1 | 0.08 | 0.01 | 0.03 | >10 |
| 27 | 24 | 0.0003 | >10 | 0.005 | >0.1 | >0.05 | >0.05 | >0.1 | >0.1 | 0.1 | 0.003 | 0.01 | 3 |
| 28 | 29 | 0.002 | >10 | 0.01 | 0.1 | 0.03 | >0.05 | >0.1 | >0.1 | 0.2 | 0.01 | 0.03 | >10 |

The compounds of this invention are generally embodied into a form suitable for convenient application. For example, the compounds can be embodied into pesticidal compositions which are provided in the form of emulsions, suspensions, solutions, dusts, and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite; diatomite; gypsum clays; propellants, such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present composition can vary within rather wide limits, ordinarily the pesticide compound will comprise between about 0.01 and about 80% by weight of the composition.

What is claimed is:

1. A compound having the formula

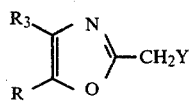

in which R is phenyl, phenylthio, phenoxy or lower alkylthio; $R_3$ is lower alkyl and Y is chloro or bromo, provided that when R is isopropylthio, $R_3$ is a lower alkyl group containing from 1 to 3 carbon atoms.

2. A process for producing a compound as defined in claim 1 comprising reacting a methyl ketone oxime having the formula

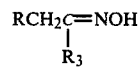

with between a two-fold and a ten-fold stoichiometric excess of chloroacetyl chloride or bromide in the absence of an acid acceptor.

3. A process for producing a compound having the formula

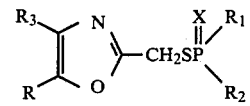

in which R is phenyl, phenylthio, phenoxy or lower alkylthio; $R_1$ is lower alkoxy; $R_2$ is lower alkyl or lower alkoxy; $R_3$ is lower alkyl and X is sulfur or oxygen; provided that when R is isopropylthio, $R_3$ is a lower alkyl group containing from 1 to 3 carbon atoms, comprising:

(a) reacting a methyl ketone oxime having the formula

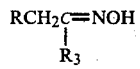

with between a two-fold and a ten-fold stoichiometric excess of chloroacetyl chloride or bromide in the absence of an acid acceptor; and (b) reacting the product of step (a) with an alkali metal salt of an acid having the formula

* * * * *

UNITED STATES PATENT AND TRADEMARK OFFICE
CERTIFICATE OF CORRECTION

PATENT NO. : 4,176,121                    Page 1 of 2
DATED     : November 27, 1979
INVENTOR(S) : Arnold D. Gutman It is certified that error appears in the above-identified patent and that said Letters Patent are hereby corrected as shown below:

Column 1, the second formula, under the heading "Summary of the Invention", should read

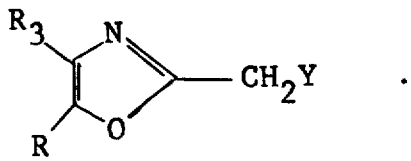

Column 2, the second part of the formula (after the arrow) should read

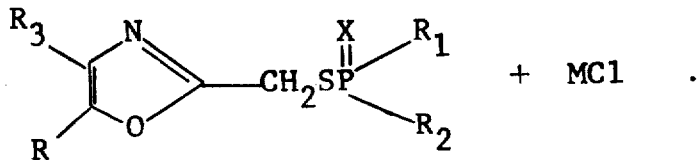     + MCl .

UNITED STATES PATENT AND TRADEMARK OFFICE
CERTIFICATE OF CORRECTION

PATENT NO. : 4,176,121

DATED : November 27, 1979

INVENTOR(S) : Arnold D. Gutman

It is certified that error appears in the above-identified patent and that said Letters Patent are hereby corrected as shown below:

Column 3, Example 2, item B, please change "2chloromethyl" to read "2-chloromethyl".

Column 3, Example 2, item B, please change ...1,3oxazole... to read ---1,3-oxazole---.

Column 5, line 48, please change ---bttom--- to read ---bottom---

Column 6, line 1, please change ---Myzur--- to read ---Myzus---.

Column 6, line 39, please change ---Druryl--- to read ---Drury---

Column 6, last line, delete the word ---terms---.

Column 7, line 4, please change the word ---terns--- to read ---terms---.

Table III, Compound 7 under heading LB, please change "0.5" to read "0.05".

Table III, Compound 12 under heading SMC, please change "0.3" to read "0.03".

Table III, Compound 14 under heading EGGS, please change "0.0005" to read "0.005".

Signed and Sealed this

Fifteenth Day of December 1981

[SEAL]

Attest:

GERALD J. MOSSINGHOFF

Attesting Officer

Commissioner of Patents and Trademarks